Figure 1:
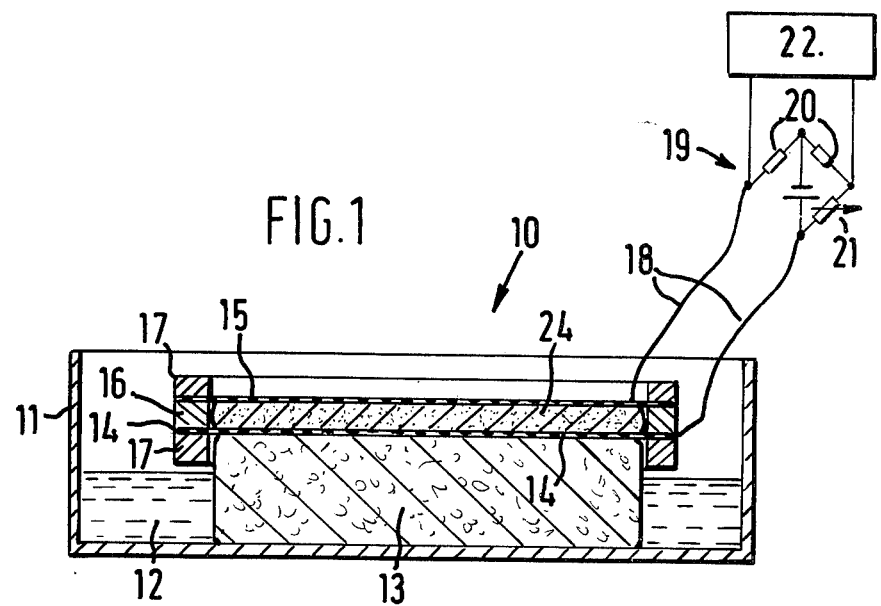

United States Patent [19]

Bushman

[11] 4,326,200

[45] Apr. 20, 1982

[54] GAS DETECTING AND MEASURING APPARATUS

[75] Inventor: John A. Bushman, London, England

[73] Assignee: Neotronics Limited, Bishops Stortford, England

[21] Appl. No.: 149,525

[22] Filed: May 13, 1980

[30] Foreign Application Priority Data

May 18, 1979 [GB] United Kingdom ............... 17380/79

[51] Int. Cl.³ .................. G08B 17/10; G01N 27/46
[52] U.S. Cl. ...................................... 340/632; 73/23; 204/195 R; 324/71 R
[58] Field of Search ........................ 340/632, 633, 634; 338/34; 73/23 R; 204/195 R, 1 K; 422/83, 88, 98; 324/71 R

[56] References Cited

U.S. PATENT DOCUMENTS

| | | | |
|---|---|---|---|
| 3,349,011 | 10/1967 | Hersch et al. | 204/1 K |
| 3,591,480 | 7/1971 | Neff et al. | 204/1 K X |
| 3,776,832 | 12/1973 | Oswin et al. | 204/1 K X |
| 3,852,169 | 12/1974 | Kring et al. | 204/1 K |
| 3,878,080 | 4/1975 | Luck | 204/1 K X |
| 4,049,503 | 9/1977 | Becker et al. | 204/195 R X |
| 4,149,948 | 4/1979 | Peterson et al. | 204/195 R |
| 4,202,748 | 5/1980 | Kroneisen | 204/1 K X |
| 4,209,299 | 6/1980 | Carlson | 204/1 K X |

FOREIGN PATENT DOCUMENTS 797835 7/1958 United Kingdom .
1528183 10/1978 United Kingdom .

OTHER PUBLICATIONS

British Journal of Anaesthesia, pp. 439–442, (1975) 47; "A New Method for the Measurement of Carbon Dioxide in the Expired Air", by Bushman et al.

Primary Examiner—John W. Caldwell, Sr.
Assistant Examiner—Daniel Myer
Attorney, Agent, or Firm—William R Hinds

[57] ABSTRACT

A gas detecting device e.g. for detecting $CO_2$ in air, has a vessel containing water and a layer of ion-exchange resin wetted by the water and sandwiched between air and water-permeable electrode gauze discs. Any $CO_2$ in the ambient atmosphere dissolves in the water and the dissociated ions lower the resistance between the electrodes which may be connected to a bridge circuit adjusted to be out of balance at a predetermined $CO_2$ concentration or which may be of dissimilar metal to form a galvanic cell with a measurable output current at a predetermined $CO_2$ concentration.

12 Claims, 3 Drawing Figures

GAS DETECTING AND MEASURING APPARATUS

The present invention concerns gas detecting and measuring apparatus. Although it is not so restricted, it will hereafter be particularly described with reference to detecting the presence of, and measuring the concentration of, carbon dioxide in air so as to indicate when the concentration exceeds a threshold value.

In certain commercial and industrial environments, such as beer cellars of public houses or power stations, or when monitoring the content of flue gases there is a need for a device for detecting $CO_2$, a potentially harmful gas. Moreover, it is highly desirable that such a device should be portable, should be of relatively simple and inexpensive construction, requiring little or no special skill for its setting up, operation and maintenance, and should if possible contain no moving parts, whereby to enhance its reliability and service life.

The present invention seeks to provide gas detecting and measuring apparatus which fulfils the above requirements and which is based on the principle of detecting the gas in question by measuring the change in resistance between electrodes between which is disposed a liquid that ionizes when the gas dissolves in it. The resistance is dependent on the amount of gas dissolved in the liquid, that is to say, on the degree of ionic dissociation of the gas in the liquid. Since the amount of gas dissolved depends on the time for which the gas is in contact with the liquid, it is known to provide gas detecting apparatus operating on this principle with a de-ionizing medium.

However, some prior art gas detecting apparatus employing this principle has been used for continuous determination of the concentration of the gas and included a pump for continuously circulating the liquid between the electrodes and a de-ionizing station.

It is also known to provide a biomedical carbon dioxide sensor contained in a probe for use in in vivo or in vitro analysis; this probe has a permeable outer wall and contains an ion-selective electrode and a reference electrode in an electrolytic medium. Such probes do not, however, contain a de-ionizing medium for regenerating the electrolyte between the reference electrode and the sensing electrode.

The present invention seeks to overcome these disadvantages and accordingly, it consists in gas detecting apparatus containing no moving parts and comprising a reservoir for a liquid ionizable by dissolution therein of the gas to be detected, at least two spaced apart electrodes disposed in or adjacent the reservoir electrically connected or connectable to an external circuit for measuring the variation in electrical resistance of said liquid between the electrodes, a wettable de-ionizing medium accessible to said gas from the ambient atmosphere and disposed in such proximity to at least one of the electrodes and to the reservoir that the said medium is wetted in use by said liquid and is effective to de-ionize said liquid between the electrodes.

Preferably, said medium is disposed between and in contact with the electrodes. In a preferred embodiment, said reservoir is disposed in a vessel that has a cover plate with one or more apertures in it constituting the means allowing access of said gas.

Preferably, the external circuit includes an indicating and/or recording instrument such as a galvanometer and/or a pen recorder. An audible and/or visible alarm may be connected to the circuit.

Where an external power supply is used, the external circuit may include a bridge circuit supplied by direct current from a battery, although it may be advantageous to use a rectified and smoothed AC supply.

The electrodes are preferably in the form of a pair of metallic gauze discs spaced apart by a separator. In an advantageous embodiment, the electrodes are of dissimilar metals and form, in effect, a battery or cell, whereby to dispense with the need for an external electric power supply. This feature greatly increases the portability and safety of the device. As a further development of the last-mentioned embodiment, there are in fact three electrodes in a juxtaposed configuration of which the two end ones are made from one metallic material, e.g. stainless steel, while the third electrode is between the said end electrodes and is of a different metallic material, e.g. lead. The electrodes are preferably connected to an amplifier to raise the current above the input threshold of the indicating and/or recording instrument.

It is preferred to make the electrical connections to the gauze discs not in the form of a single point connection but rather in the form of a ring. The gauze discs are preferably made of copper but they may be made of stainless steel.

In one preferred embodiment, the electrodes are disposed in a second vessel which is mounted in the first mentioned vessel and which is apertured to allow said liquid to pass from the first vessel into it, the second vessel being substantially filled with said medium in contact with the medium between the electrodes.

This embodiment is preferable in that the need for a separate pad is eliminated and the extra mass of de-ionizing medium, i.e. ion-exchanging resin below the lower electrode sandwiching the resin with the upper electrode ensures a longer service life for the apparatus by preventing ions from escaping from the resin in the cell and migrating into the water in the reservoir.

It may be advantageous if the first vessel is sealed and pre-filled with said liquid. Furthermore, the accuracy of the instrument may be improved if the liquid is distilled water to reduce the likelihood of oxidation of the electrodes, and to reduce drift.

Most ion-exchange resins are not selectively sensitive and are therefore suitable for detecting a range of gases or mixture of gases, but of course in air carbon dioxide is the only significant component in air that dissolves in water. Nevertheless, resins may be available, or may be made by "poisoning" existing resins, for detecting other soluble and potentially harmful gases such as chlorine, sulphur dioxide or hydrogen sulphide.

Figure 2:
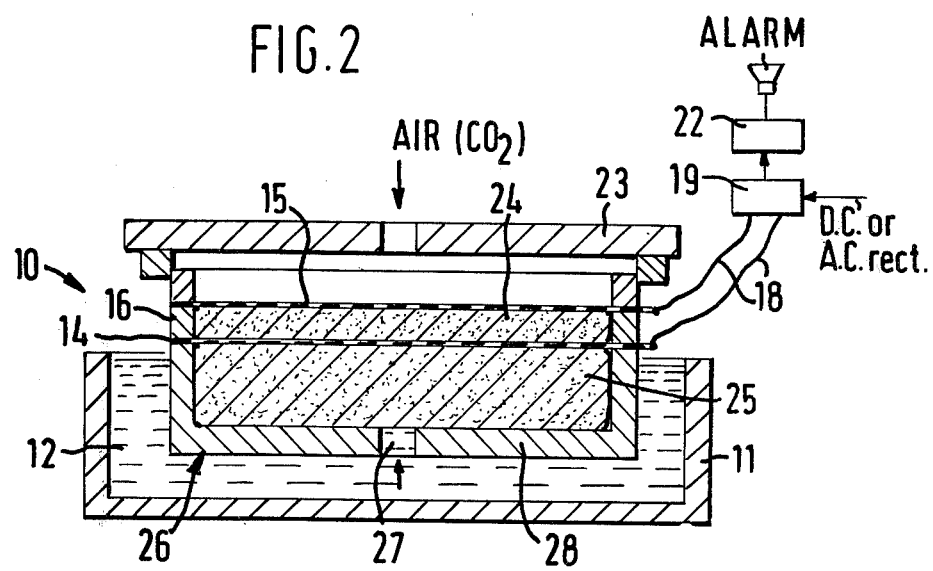
Figure 3:
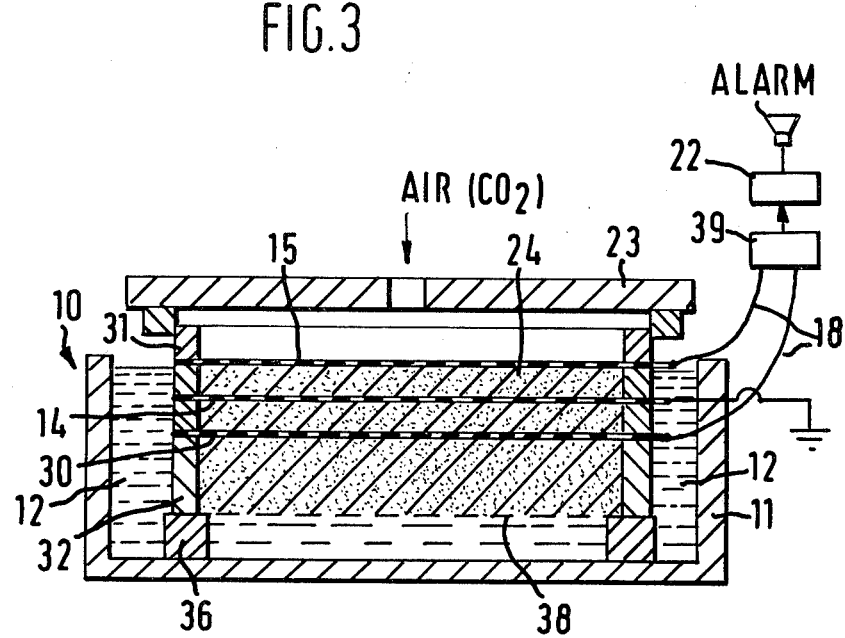

The invention is described merely by way of example, with reference to the accompanying schematic drawings, in which:

FIG. 1 is a diagrammatic cross-section of a first preferred embodiment of the invention, FIG. 2 is a view similar to FIG. 1 but illustrating a second preferred embodiment, and FIG. 3 is a view similar to FIGS. 1 and 2 but illustrating a third preferred embodiment.

Like parts have been allotted like reference numbers in the drawings.

Referring first to FIG. 1, there is provided a gas detecting instrument 10 for detecting carbon dioxide in commercial or industrial environments where there may be the risk of an accumulation of carbon dioxide above a level safe to human beings, e.g. in beer cellars, and comprising a vessel 11 containing water 12 and a centrally disposed sponge pad 13 permeable to water. On top of the pad 13 sits a measurement cell comprising a pair of electrodes 14 and 15 in the form of copper gauze discs having, typically, a diameter of 7.5 cm and a spacing, ensured by spacers 16, of 2 mm, typically. The electrodes are held in place by frame members 17 and are connected by electrical leads 18 to a Wheatstone bridge 19 containing two fixed resistors 20 of comparable resistance (e.g. 470 ohms) to that of the cell (e.g. 500 ohms) and a variable resistor 21. The output of the bridge 19 is connected to a recording/indicating instrument 22 e.g. pen recorder or a galvanometer. The vessel is provided with an apertured cover plate which is not shown in FIG. 1 (but is shown at 23 in FIG. 2) to limit the rate of evaporation of water.

The gap between the electrodes 14, 15 is filled with a mass of ion-exchanging resin 24 which is wettable by water so that in use any carbon dioxide in the ambient atmosphere finding its way between the electrodes dissolves in the water in the resin to cause ionic dissociation and a consequential decrease in resistance between the electrodes. The resin de-ionizes the liquid so that a balanced condition can be established in the bridge circuit 19 corresponding to, say, 1% carbon dioxide in the air as a threshold of carbon dioxide concentration.

It has been found that the resin 24 (e.g. one available from the Elga Company Limited). became immediately uniformly wet on contact with the water.

The embodiment shown in FIG. 2 dispenses with the sponge pad and utilizes instead a further mass of resin 25 of the same material as that of 24 and contained in a second smaller vessel 26 inside the vessel 11 which has an aperture 27 in its bottom 28 to allow water in the vessel 11 to wet the resin masses 24, 25. The cell is mounted on top of this inner vessel 26 so that water from the outer vessel 11 passes through the aperture 27 to the mass of resin 25 in the inner vessel 26 and so to the resin 24 sandwiched between the electrodes, 14,15. The apertured top plate 23 covering the top of the inner vessel is also illustrated.

Referring now to the embodiment shown in FIG. 3, an external electrical power supply is dispensed with. Instead the electrodes 14,15 are made of dissimilar metal, e.g. lead and stainless steel respectively, so as to form a galvanic cell. A third electrode 30, of the same material as electrode 15, is also added. The electrodes are spaced apart by inert plastics annular members 31, e.g. of methyl methacrylate, and supported by support members 32, 36 which may also be of methyl methacrylate. A mesh e.g. of nylon, supports the resin 24.

The lead electrode 14 is earthed and the stainless steel electrodes 15,30 are connected by leads 18 to an amplifier 39 to raise the cell output above the input threshold of the instrument 22. The amplifier 39 may be a 741 type operational amplifier with a gain of ten. Clearly the presence of the gas to be detected causes ionization and consequent changes in the cell resistance and thus in the cell current (or voltage) output.

Although in FIG. 3 the apertured lid 23 has again been shown, its presence is optional.

It has been found that the detector according to FIG. 3 has improved characteristics as regards drift and settling time.

To reduce the settling time and drift of the apparatus as described it may be preferable to use distilled and de-ionized water; to eliminate or reduce polarization from the electrodes in the embodiments of FIG. 1 or FIG. 2 it may be preferred to use a rectified AC bridge.

A source of inaccuracy may be due to oxidation at the soldered joints between the leads and the gauze discs and this may be reduced by using a continuous ring or annular contact on each gauze.

For certain uses, the cell may be sale after being prefilled with water. The gas inlet hole may have a filter placed before it to remove certain undesired constituents of the ambient atmosphere but this may have a disadvantageous effect on the response time of the instrument. The bridge circuit in FIGS. 1 and 2 and the amplifier of FIG. 3 may be connected to a suitable alarm circuit (not shown) connected to an output device emitting a visible and/or audible alarm when the concentration of the gas being detected or monitored exceeds a threshold value.

The apparatus according to the preferred embodiments exhibits good linearity of response in the range up to 2% $CO_2$.

It is conceivable in certain embodiments for the ion-exchange resin to be contiguous with the electrodes but not to be disposed between them.

What is claimed is:

1. Gas detecting apparatus containing no moving parts and comprising a reservoir for a liquid ionizable by dissolution therein of the gas to be detected, at least two spaced apart electrodes disposed at least adjacent the reservoir for electrical connection to an external circuit for measuring the variation in electrical resistance of said liquid between the electrodes, a wettable de-ionizing medium accessible to said gas from the ambient atmosphere and disposed in such proximity to at least one of the electrodes and to the reservoir that the said medium is wetted in use by said liquid and is effective to de-ionize said liquid between the electrodes.

2. Apparatus according to claim 1, wherein said medium is disposed between and in contact with the electrodes.

3. Apparatus according to claim 2, wherein said external circuit includes a recording instrument for recording said electrical resistance of said liquid between said electrodes.

4. Apparatus according to claim 2, wherein the electrodes are in the form of metallic gauze discs separated by said medium.

5. Apparatus according to claim 2, wherein the apparatus includes a vessel defining said reservoir, a cover plate for said vessel, said cover plate being apertured to allow said medium to be accessible to said gas.

6. Apparatus according to claim 5, wherein the electrodes are disposed in a second vessel which is mounted in the first-mentioned vessel and which is apertured to allow said liquid to pass from the first vessel into the second vessel, the second vessel being substantially filled with said medium in contact with the medium between the electrodes.

7. Apparatus according to claim 2, wherein said electrodes are of dissimilar metallic material and form a galvanic cell unconnected to any external electric power supply.

8. Apparatus according to claim 7, wherein there are three of said electrodes in a sandwich-like arrangement, the central electrode being of a material different to the two end electrodes which are of the same material.

9. Apparatus according to claim 8, wherein the central electrode is earthed and the end electrodes are connected to an amplifier.

10. Apparatus according to claim 2, wherein the electrodes and the medium therebetween form a measuring cell supported on a sponge pad mounted in the reservoir.

11. Apparatus according to claim 2 wherein said medium is constituted by a mass of ion-exchanging resin.

12. Apparatus according to claim 1 wherein said medium is constituted by a mass of ion-exchanging resin, and said electrodes are disposed contiguously to said reservoir.

* * * * *